US008948407B2

(12) United States Patent
Alderson et al.

(10) Patent No.: US 8,948,407 B2
(45) Date of Patent: Feb. 3, 2015

(54) BANDLIMITING ANTI-NOISE IN PERSONAL AUDIO DEVICES HAVING ADAPTIVE NOISE CANCELLATION (ANC)

(75) Inventors: Jeffrey Alderson, Austin, TX (US); Nitin Kwatra, Austin, TX (US); Gautham Devendra Kamath, Austin, TX (US); Ali Abdollahzadeh Milani, Austin, TX (US); John L. Melanson, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 318 days.

(21) Appl. No.: 13/333,484

(22) Filed: Dec. 21, 2011

(65) Prior Publication Data

US 2012/0308024 A1 Dec. 6, 2012

Related U.S. Application Data

(60) Provisional application No. 61/493,162, filed on Jun. 3, 2011.

(51) Int. Cl.
*A61F 11/06* (2006.01)
*G10K 11/178* (2006.01)

(52) U.S. Cl.
CPC .......... *G10K 11/178* (2013.01); *G10K 11/1784* (2013.01); *G10K 2210/108* (2013.01);
(Continued)

(58) Field of Classification Search
CPC .................. G10K 15/02; G10K 15/04; G10K 2210/1081; G10K 2210/11; G10K 2210/119; G10K 2210/1291; G10K 2210/3012; G10K 2210/3014; G10K 2210/3017; G10K 2210/30231; G10K 2210/30232; G10K 2210/3026; G10K 2210/3028; G10K 2210/30281; G10K 2210/3029; G10K 2210/3031; G10K 2210/3035; G10K 2210/3036; G10K 2210/3045; G10K 2210/3048; G10K 2210/3049; G10K 2210/3055; G10K 2210/3056; G10K 2210/3057; G10K 2210/3221; G10K 2210/3225; G10K 2210/3226; G10K 2210/505; H04R 2460/01; H04M 3/002; H04M 3/18
USPC ............ 381/13, 71.1–71.12, 73.1, 74, 83, 86, 381/302, 92, 93, 94.1–94.4, 94.7, 94.8, 381/94.9, 95, 96, 97, 98, 122, 119; 704/E21.014, 233, E19.014, E21.002; 455/570; 379/406.01–406.15
See application file for complete search history.

(56) References Cited

U.S. PATENT DOCUMENTS 5,251,263 A 10/1993 Andrea et al.
5,337,365 A 8/1994 Hamabe et al.
(Continued)

FOREIGN PATENT DOCUMENTS

EP 1880699 A2 1/2008
EP 2395500 A1 12/2011
(Continued)

OTHER PUBLICATIONS

U.S. Appl. No. 13/686,353, filed Nov. 27, 2012, Hendrix, et al.
(Continued)

*Primary Examiner* — Leshui Zhang
(74) *Attorney, Agent, or Firm* — Mitch Harris, Atty at Law, LLC; Andrew M. Harris

(57) ABSTRACT

A personal audio device, such as a wireless telephone, includes noise canceling circuit that adaptively generates an anti-noise signal from a reference microphone signal and injects the anti-noise signal into the speaker or other transducer output to cause cancellation of ambient audio sounds. An error microphone may also be provided proximate the speaker to measure the output of the transducer in order to control the adaptation of the anti-noise signal and to estimate an electro-acoustical path from the noise canceling circuit through the transducer. A processing circuit that performs the adaptive noise canceling (ANC) function also either adjusts the frequency response of the anti-noise signal with respect to the reference microphone signal, and/or by adjusting the response of the adaptive filter independent of the adaptation provided by the reference microphone signal.

9 Claims, 9 Drawing Sheets

(52) U.S. Cl.
CPC .................. *G10K2210/1081* (2013.01); *G10K 2210/3017* (2013.01); *G10K 2210/3028* (2013.01); *G10K 2210/3035* (2013.01); *G10K 2210/3049* (2013.01); *G10K 2210/3056* (2013.01); *G10K 2210/511* (2013.01); *G10K 2210/1082* (2013.01)
USPC .............. 381/71.11; 381/13; 381/83; 381/92; 381/98; 704/E21.014; 455/570; 379/406.12

(56) References Cited

U.S. PATENT DOCUMENTS

| | | | |
|---|---|---|---|
| 5,410,605 | A | 4/1995 | Sawada et al. |
| 5,425,105 | A | 6/1995 | Lo et al. |
| 5,586,190 | A | 12/1996 | Trantow et al. |
| 5,640,450 | A | 6/1997 | Watanabe |
| 5,699,437 | A | 12/1997 | Finn |
| 5,706,344 | A | 1/1998 | Finn |
| 5,768,124 | A | 6/1998 | Stothers et al. |
| 5,815,582 | A | 9/1998 | Claybaugh et al. |
| 5,946,391 | A | 8/1999 | Dragwidge et al. |
| 5,991,418 | A | 11/1999 | Kuo |
| 6,041,126 | A | 3/2000 | Terai et al. |
| 6,118,878 | A | 9/2000 | Jones |
| 6,219,427 | B1 | 4/2001 | Kates et al. |
| 6,418,228 | B1 | 7/2002 | Terai et al. |
| 6,434,246 | B1 | 8/2002 | Kates et al. |
| 6,434,247 | B1 | 8/2002 | Kates et al. |
| 6,768,795 | B2 | 7/2004 | Feltstrom et al. |
| 6,850,617 | B1 | 2/2005 | Weigand |
| 7,103,188 | B1 | 9/2006 | Jones |
| 7,181,030 | B2 | 2/2007 | Rasmussen et al. |
| 7,330,739 | B2 | 2/2008 | Somayajula |
| 7,365,669 | B1 | 4/2008 | Melanson |
| 7,742,790 | B2 | 6/2010 | Konchitsky et al. |
| 8,019,050 | B2 | 9/2011 | Mactavish et al. |
| 8,249,262 | B2 | 8/2012 | Chua et al. |
| 8,290,537 | B2 | 10/2012 | Lee et al. |
| 8,379,884 | B2 | 2/2013 | Horibe et al. |
| 8,401,200 | B2 | 3/2013 | Tiscareno et al. |
| 2001/0053228 | A1 | 12/2001 | Jones |
| 2002/0003887 | A1 | 1/2002 | Zhang et al. |
| 2004/0165736 | A1 | 8/2004 | Hetherington et al. |
| 2004/0167777 | A1 | 8/2004 | Hetherington et al. |
| 2004/0264706 | A1 | 12/2004 | Ray et al. |
| 2005/0117754 | A1 | 6/2005 | Sakawaki |
| 2005/0240401 | A1 | 10/2005 | Ebenezer |
| 2006/0153400 | A1 | 7/2006 | Fujita et al. |
| 2007/0030989 | A1 | 2/2007 | Kates |
| 2007/0033029 | A1 | 2/2007 | Sakawaki |
| 2007/0038441 | A1 | 2/2007 | Inoue et al. |
| 2007/0053524 | A1 | 3/2007 | Haulick et al. |
| 2007/0076896 | A1 | 4/2007 | Hosaka et al. |
| 2007/0154031 | A1 | 7/2007 | Avendano et al. |
| 2007/0258597 | A1 | 11/2007 | Rasmussen et al. |
| 2007/0297620 | A1 | 12/2007 | Choy |
| 2008/0019548 | A1 | 1/2008 | Avendano |
| 2008/0181422 | A1 | 7/2008 | Christoph |
| 2008/0226098 | A1 | 9/2008 | Haulick et al. |
| 2009/0012783 | A1 | 1/2009 | Klein |
| 2009/0034748 | A1 | 2/2009 | Sibbald |
| 2009/0041260 | A1 | 2/2009 | Jorgensen et al. |
| 2009/0046867 | A1 | 2/2009 | Clemow |
| 2009/0196429 | A1 | 8/2009 | Ramakrishnan et al. |
| 2009/0220107 | A1 | 9/2009 | Every et al. |
| 2009/0238369 | A1 | 9/2009 | Ramakrishnan et al. |
| 2009/0245529 | A1 | 10/2009 | Asada et al. |
| 2009/0254340 | A1 | 10/2009 | Sun et al. |
| 2009/0290718 | A1 | 11/2009 | Kahn et al. |
| 2009/0296965 | A1 | 12/2009 | Kojima |
| 2009/0304200 | A1 | 12/2009 | Kim et al. |
| 2010/0014683 | A1 | 1/2010 | Maeda et al. |
| 2010/0014685 | A1 | 1/2010 | Wurm |
| 2010/0061564 | A1 | 3/2010 | Clemow et al. |
| 2010/0069114 | A1 | 3/2010 | Lee et al. |
| 2010/0082339 | A1 | 4/2010 | Konchitsky et al. |
| 2010/0098263 | A1 | 4/2010 | Pan et al. |
| 2010/0124335 | A1 | 5/2010 | Wessling et al. |
| 2010/0124336 | A1 | 5/2010 | Shridhar et al. |
| 2010/0166203 | A1 | 7/2010 | Peissig et al. |
| 2010/0195838 | A1 | 8/2010 | Bright |
| 2010/0195844 | A1 | 8/2010 | Christoph et al. |
| 2010/0272283 | A1 | 10/2010 | Carreras et al. |
| 2010/0274564 | A1 | 10/2010 | Bakalos et al. |
| 2010/0296666 | A1 | 11/2010 | Lin |
| 2010/0296668 | A1 | 11/2010 | Lee et al. |
| 2010/0310086 | A1 | 12/2010 | Magrath et al. |
| 2010/0322430 | A1 | 12/2010 | Isberg |
| 2011/0007907 | A1 | 1/2011 | Park et al. |
| 2011/0106533 | A1 | 5/2011 | Yu |
| 2011/0142247 | A1 | 6/2011 | Fellers et al. |
| 2011/0144984 | A1 | 6/2011 | Konchitsky |
| 2011/0158419 | A1 | 6/2011 | Theverapperuma et al. |
| 2011/0222698 | A1 | 9/2011 | Asao et al. |
| 2011/0249826 | A1 | 10/2011 | Van Leest |
| 2011/0288860 | A1 | 11/2011 | Schevciw et al. |
| 2011/0293103 | A1 | 12/2011 | Park et al. |
| 2011/0299695 | A1* | 12/2011 | Nicholson .................... 381/71.6 |
| 2011/0317848 | A1 | 12/2011 | Ivanov et al. |
| 2012/0135787 | A1 | 5/2012 | Kusunoki et al. |
| 2012/0140943 | A1 | 6/2012 | Hendrix et al. |
| 2012/0207317 | A1 | 8/2012 | Abdollahzadeh Milani et al. |
| 2012/0250873 | A1 | 10/2012 | Bakalos et al. |
| 2012/0259626 | A1 | 10/2012 | Li et al. |
| 2012/0300958 | A1 | 11/2012 | Klemmensen |
| 2012/0308021 | A1 | 12/2012 | Kwatra et al. |
| 2012/0308025 | A1 | 12/2012 | Hendrix et al. |
| 2012/0308026 | A1 | 12/2012 | Kamath et al. |
| 2012/0308027 | A1 | 12/2012 | Kwatra |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0177851 | A1 | 6/2014 | Kitazawa et al. |

FOREIGN PATENT DOCUMENTS

| | | | |
|---|---|---|---|
| GB | 2401744 | A | 11/2004 |
| GB | 2455821 | A | 6/2009 |
| GB | 2455824 | A | 6/2009 |
| GB | 2455828 | A | 6/2009 |
| JP | H06-186985 | A | 7/1994 |
| WO | WO 03/015074 | A1 | 2/2003 |
| WO | WO 2007007916 | A1 | 1/2007 |
| WO | WO 2007113487 | A1 | 11/2007 |
| WO | WO 2010117714 | A1 | 10/2010 |
| WO | WO 2012134874 | A1 | 10/2012 |

OTHER PUBLICATIONS

U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.

(56) References Cited

OTHER PUBLICATIONS

Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-III 928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/029,159, filed Sep. 17, 2013, Li, et al.
U.S. Appl. No. 14/062,951, filed Oct. 25, 2013, Zhou, et al.
U.S. Appl. No. 13/968,007, filed Aug. 15, 2013, Hendrix, et al.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
U.S. Appl. No. 14/197,814, filed Mar. 5, 2014, Kaller et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
U.S. Appl. No. 14/197,814, filed Mar. 5, 2014, Kaller, et al.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-3 in pdf), Pensacola, FL, US.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.

(56) References Cited

OTHER PUBLICATIONS

Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages, (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.

* cited by examiner

BANDLIMITING ANTI-NOISE IN PERSONAL AUDIO DEVICES HAVING ADAPTIVE NOISE CANCELLATION (ANC)

This U.S. patent application Claims priority under 35 U.S.C. 119(e) to U.S. Provisional Patent Application Ser. No. 61/493,162 filed on Jun. 3, 2011.

BACKGROUND OF THE INVENTION

1. Field of the Invention

The present invention relates generally to personal audio devices such as wireless telephones that include noise cancellation, and more specifically, to a personal audio device in which the anti-noise signal is band-limited to make the ANC operation more effective.

2. Background of the Invention

Wireless telephones, such as mobile/cellular telephones, cordless telephones, and other consumer audio devices, such as MP3 players and headphones or earbuds, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Since the acoustic environment around personal audio devices such as wireless telephones can change dramatically, depending on the sources of noise that are present and the position of the device itself, it is desirable to adapt the noise canceling to take into account such environmental changes. However, adaptive noise canceling circuits can be complex, consume additional power and can generate undesirable results under certain circumstances.

Therefore, it would be desirable to provide a personal audio device, including a wireless telephone, that provides noise cancellation in a variable acoustic environment.

SUMMARY OF THE INVENTION

The above stated objective of providing a personal audio device providing noise cancellation in a variable acoustic environment, is accomplished in a personal audio device, a method of operation, and an integrated circuit. The method is a method of operation of the personal audio device and the integrated circuit, which can be incorporated within the personal audio device.

The personal audio device includes a housing, with a transducer mounted on the housing for reproducing an audio signal that includes both source audio for playback to a listener and an anti-noise signal for countering the effects of ambient audio sounds in an acoustic output of the transducer. A reference microphone is mounted on the housing to provide a reference microphone signal indicative of the ambient audio sounds. The personal audio device further includes an adaptive noise-canceling (ANC) processing circuit within the housing for adaptively generating an anti-noise signal from the reference microphone signal such that the anti-noise signal causes substantial cancellation of the ambient audio sounds. An error microphone is included for controlling the adaptation of the anti-noise signal to cancel the ambient audio sounds and for correcting for the electro-acoustic path from the output of the processing circuit through the transducer. The ANC processing circuit avoids generating anti-noise that is disruptive, ineffective or that compromises performance in certain frequency ranges by shaping a frequency response of the anti-noise to the reference microphone signal and/or by adjusting a response of the adaptive filter independent of the adaptive control with respect to the reference microphone signal.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise canceling techniques and circuits that can be implemented in a personal audio device, such as a wireless telephone. The personal audio device includes an adaptive noise canceling (ANC) circuit that measures the ambient acoustic environment and generates an adaptive anti-noise signal that is injected in the speaker (or other transducer) output to cancel ambient acoustic events. A reference microphone is provided to measure the ambient acoustic environment and an error microphone is be included to control adaptation of the anti-noise signal to cancel the ambient acoustic events and to provide estimation of an electro-acoustical path from the output of the ANC circuit through the speaker. The ANC processing circuit avoids generating anti-noise that is disruptive, ineffective or that compromises performance in certain frequency ranges by shaping a frequency response of the anti-noise to the reference microphone signal and/or by adjusting a response of the adaptive filter independent of the adaptive control with respect to the error microphone signal.

Figure 1:
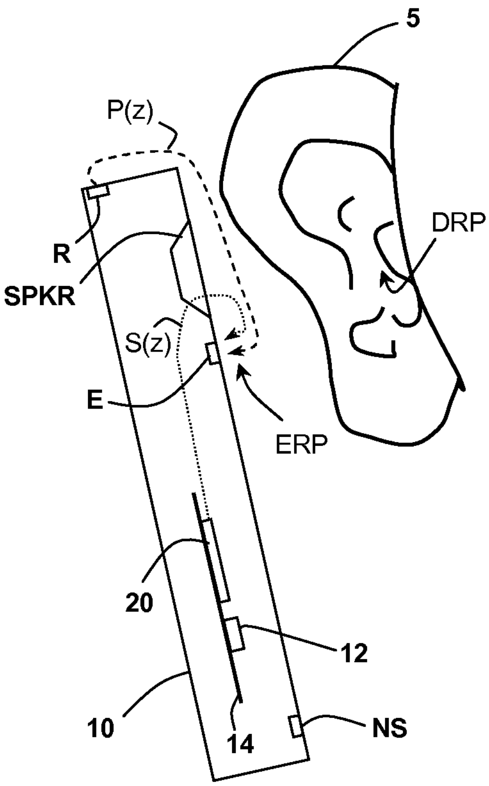
FIG. 1 is an illustration of a wireless telephone 10 in accordance with an embodiment of the present invention.

Referring now to FIG. 1, a wireless telephone 10 is illustrated in accordance with an embodiment of the present invention is shown in proximity to a human ear 5. Illustrated wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the invention recited in the Claims. Wireless telephone 10 includes a transducer such as speaker SPKR that reproduces distant speech received by wireless telephone 10, along with other local audio event such as ringtones, stored audio program material, injection of near-end speech (i.e., the speech of the user of wireless telephone 10) to provide a balanced conversational perception, and other audio that requires reproduction by wireless telephone 10, such as sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment, and is positioned away from the typical position of a user's mouth, so that the near-end speech is minimized in the signal produced by reference microphone R. A third microphone, error microphone E is provided in order to further improve the ANC operation by providing a measure of the ambient audio combined with the audio reproduced by speaker SPKR close to ear 5 at an error microphone reference position ERP, when wireless telephone 10 is in close proximity to ear 5. Exemplary circuits 14 within wireless telephone 10 include an audio CODEC integrated circuit 20 that receives the signals from reference microphone R, near speech microphone NS and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques of the present invention measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events at error microphone E, i.e. at error microphone reference position ERP. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which is affected by the proximity and structure of ear 5 and other physical objects and human head structures that may be in proximity to wireless telephone 10, when wireless telephone is not firmly pressed to ear 5. Since the user of wireless telephone 10 actually hears the output of speaker SPKR at a drum reference position DRP, differences between the signal produced by error microphone E and what is actually heard by the user are shaped by the response of the ear canal, as well as the spatial distance between error microphone reference position ERP and drum reference position DRP. At higher frequencies, the spatial differences lead to multi-path nulls that reduce the effectiveness of the ANC system, and in some cases may increase ambient noise. While the illustrated wireless telephone 10 includes a two microphone ANC system with a third near speech microphone NS, some aspects of the present invention may be practiced in a system that does not include separate error and reference microphones, or a wireless telephone uses near speech microphone NS to perform the function of the reference microphone R. Also, in personal audio devices designed only for audio playback, near speech microphone NS will generally not be included, and the near-speech signal paths in the circuits described in further detail below can be omitted, without changing the scope of the invention.

Figure 2:
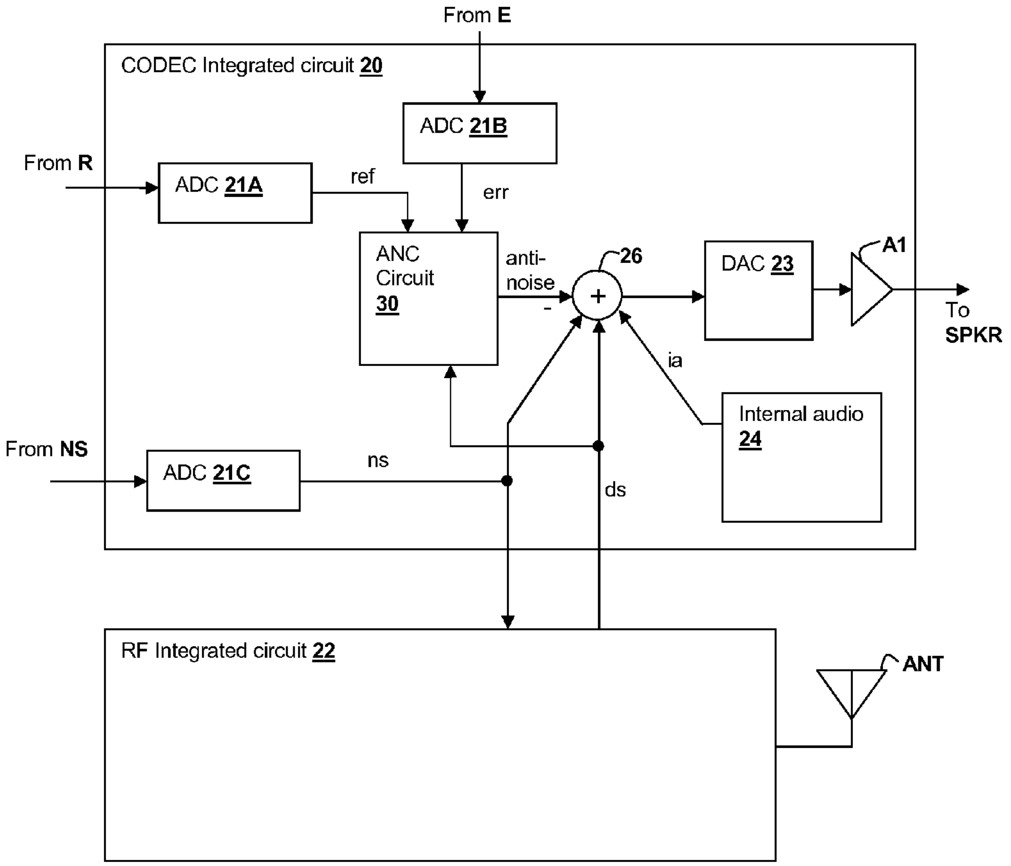
FIG. 2 is a block diagram of circuits within wireless telephone 10 in accordance with an embodiment of the present invention.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the near speech microphone signal. CODEC IC 20 generates an output for driving speaker SPKR from an amplifier A1, which amplifies the output of a digital-to-analog converter (DAC) 23 that receives the output of a combiner 26. Combiner 26 combines audio signals is from internal audio sources 24, the anti-noise signal generated by ANC circuit 30, which by convention has the same polarity as the noise in reference microphone signal ref and is therefore subtracted by combiner 26, a portion of near speech microphone signal ns so that the user of wireless telephone 10 hears their own voice in proper relation to downlink speech ds, which is received from radio frequency (RF) integrated circuit 22 and is also combined by combiner 26. Near speech microphone signal ns is also provided to RF integrated circuit 22 and is transmitted as uplink speech to the service provider via antenna ANT.

Figure 3A:
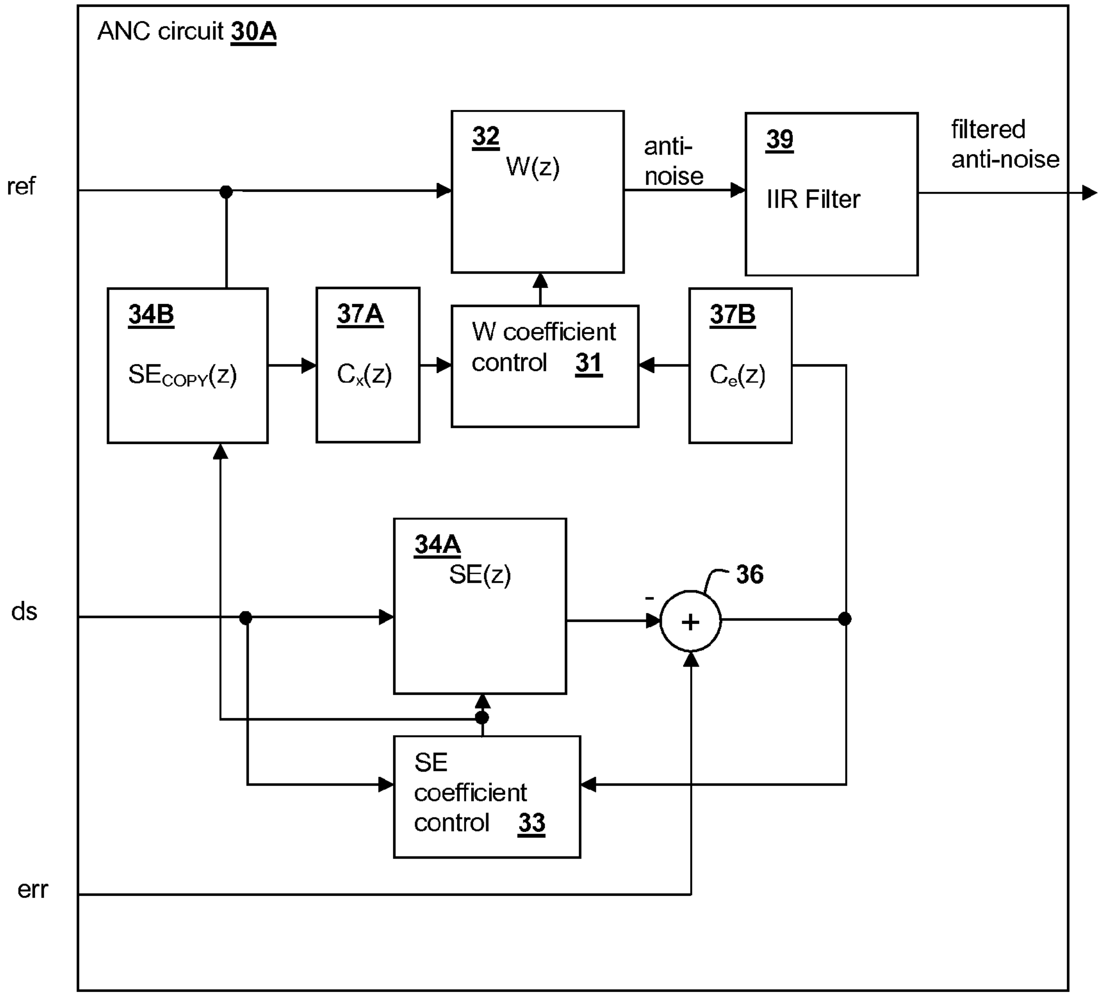
FIGS. 3A-3E are block diagrams depicting signal processing circuits and functional blocks within ANC circuit 30 of CODEC integrated circuit 20 of FIG. 2 in accordance with various embodiments of the present invention.

Referring now to FIG. 3A, details of an ANC circuit 30A are shown in accordance with an embodiment of the present invention that may be used to implement ANC circuit 30 of FIG. 2. Adaptive filter 32 receives reference microphone signal ref and under ideal circumstances, adapts its transfer function W(z) to be P(z)/S(z) to generate the anti-noise signal. The coefficients of adaptive filter 32 are controlled by a W coefficient control block 31 that uses a correlation of two signals to determine the response of adaptive filter 32, which generally minimizes, in a least-mean squares sense, those components of reference microphone signal ref that are present in error microphone signal err. The signals provided as inputs to W coefficient control block 31 are the reference microphone signal ref as shaped by a copy of an estimate of the response of path S(z) provided by filter 34B and another signal provided from the output of a combiner 36 that includes error microphone signal err. By transforming reference microphone signal ref with a copy of the estimate of the response of path S(z), $SE_{COPY}(z)$, and minimizing the portion of the error signal that correlates with components of reference microphone signal ref, adaptive filter 32 adapts to the desired response of P(z)/S(z). A filter 37A that has a response $C_x(z)$ as explained in further detail below, processes the output of filter 34B and provides the first input to W coefficient control block 31. The second input to W coefficient control block 31 is processed by another filter 37B having a response of $C_e(z)$. Response $C_e(z)$ has a phase response matched to response $C_x(z)$ of filter 37A. The input to filter 37B includes error microphone signal err and an inverted amount of downlink audio signal ds that has been processed by filter response SE(z), of which response $SE_{COPY}(z)$ is a copy. Combiner 36 combines error microphone signal err and the inverted downlink audio signal ds. By injecting an inverted amount of downlink audio signal ds adaptive filter 32 is prevented from adapting to the relatively large amount of downlink audio present in error microphone signal err and by transforming that inverted copy of downlink audio signal ds with the estimate of the response of path S(z), the downlink audio that is removed from error microphone signal err before comparison should match the expected version of downlink audio signal ds reproduced at error microphone signal err, since the electrical and acoustical path of S(z) is the path taken by downlink audio signal ds to arrive at error microphone E.

To implement the above, adaptive filter 34A has coefficients controlled by SE coefficient control block 33, which updates based on correlated components of downlink audio signal ds and an error value. The error value represents error microphone signal err after removal of the above-described filtered downlink audio signal ds, which has been previously filtered by adaptive filter 34A to represent the expected downlink audio delivered to error microphone E. The filtered version of downlink audio signal ds is removed from the output of adaptive filter 34A by combiner 36. SE coefficient control block 33 correlates the actual downlink speech signal ds with the components of downlink audio signal ds that are present in error microphone signal err. Adaptive filter 34A is thereby adapted to generate a signal from downlink audio signal ds, that when subtracted from error microphone signal err, contains the content of error microphone signal err that is not due to downlink audio signal ds.

Under certain circumstances, the anti-noise signal provided from adaptive filter 32 may contain more energy at certain frequencies due to ambient sounds at other frequencies, because W coefficient control block 31 has adjusted the frequency response of adaptive filter 32 to suppress the more energetic signals, while allowing the gain of other regions of the frequency response of adaptive filter 32 to rise, leading to a boost of the ambient noise, or "noise boost", in the other regions of the frequency response. In particular, noise boost is problematic when coefficient control block 31 has adjusted the frequency response of adaptive filter 32 to suppress more energetic signals in higher frequency ranges, e.g., between 2 kHz and 5 kHz, where multi-path nulls in paths P(z) and S(z) generally arise and the frequency response of the canal of the user's ear 5, starts to contribute to the overall operation of the ANC system as perceived by the listener. Since the phase of the anti-noise signal may not match the phase of the ambient audio sounds at drum reference position DRP in these upper frequency ranges, the anti-noise signal may actually increase noise perceived by the listener, and noise boost may compound the problem. Therefore, ANC circuit 30A includes an additional infinite impulse response (IIR) filter 39 to filter the anti-noise signal before the anti-noise signal is combined with downlink speech ds and sent to speaker SPKR. Filter 39 may alternatively be another type of filter such as a finite impulse response (FIR) filter. Filter 39 may be a low-pass filter that passes only generated anti-noise below a certain frequency, e.g., 2 kHz, or alternatively, filter 39 may be a notch filter that suppresses a particular problem frequency, e.g., a known frequency at which a multi-path null is present due to the acoustical length of path P(z) so that the phase of the anti-noise signal is incorrect. In accordance with another embodiment of the invention, filter 39 may be a high-pass filter that removes problematic low-frequency anti-noise components, or filter 39 may be a bandpass filter. Filter 39 removes the anti-noise either above the cut-off frequency of filter 39 when a low-pass filter response is used, below the cut-off frequency of filter 39 when a high-pass filter is used, removes the region of problem frequencies when a notch filter response is used, or removes both low and high ranges outside of a passband when a bandpass filter is used. The notch filter response could also include multiple nulls, in order to shape the frequencies present in the anti-noise signal to remove problem spot frequencies. ANC circuit 30A of FIG. 3A is an example of a circuit that adjusts the frequency response of the anti-noise signal with respect to reference microphone signal ref. In order to preserve stability in the output of W coefficient control 31, response $C_x(z)$ of filter 37A includes a copy of the response of filter 39. A low-pass characteristic is provided in each of filters 37A and 37B so that the action of W coefficient control 31 does not attempt to counteract the processing performed by filter 39 by adapting response W(z) of adaptive filter 32.

Figure 3B:
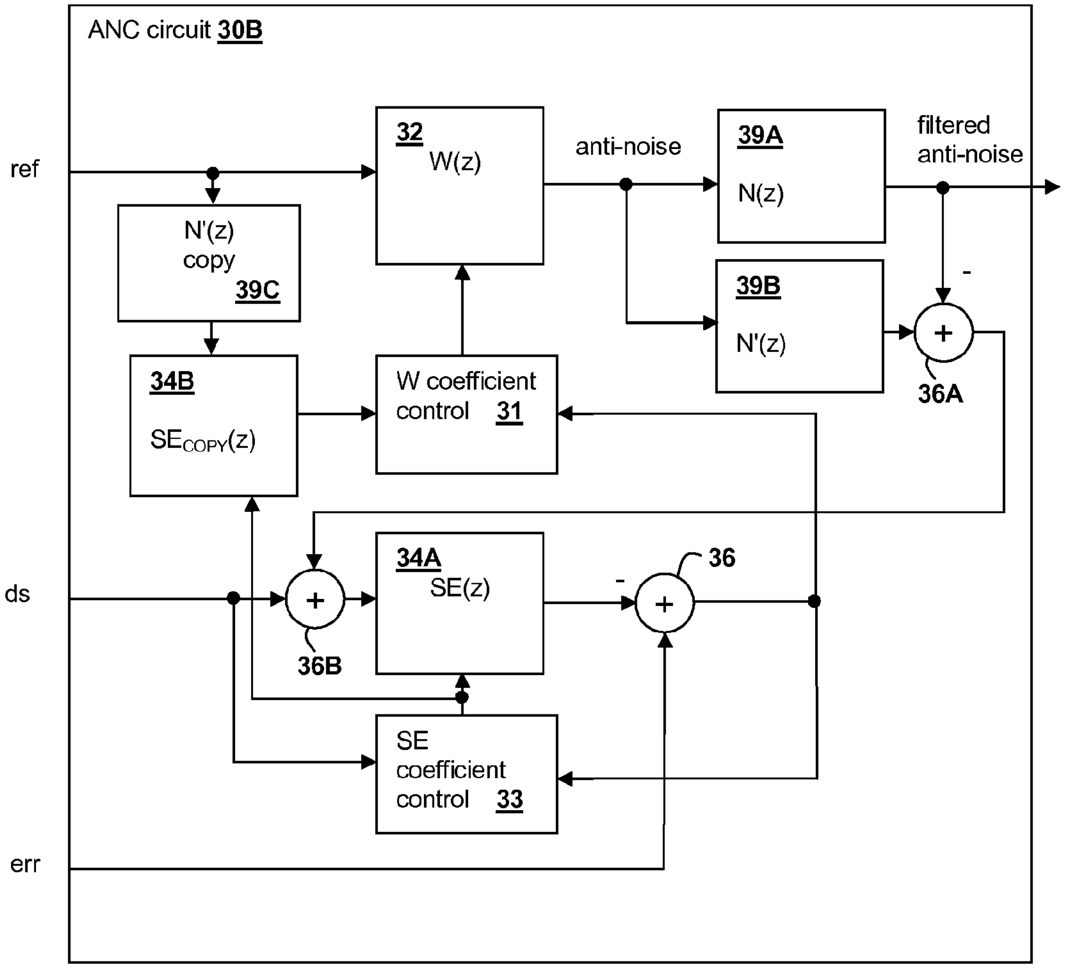

Referring now to FIG. 3B, details of another ANC circuit 30B are shown in accordance with an alternative embodiment of the present invention that may be used to implement ANC circuit 30 of FIG. 2. ANC circuit 30B is similar to ANC circuit 30A of FIG. 3A, so only differences between them will be described below. In ANC circuit 30B, the anti-noise output of adaptive filter 32 is filtered, while allowing W coefficient control block 31 to adapt just as the anti-noise signal was not filtered, a first notch filter 39A removes certain frequencies from the anti-noise signal, but a second all-pass filter 39B having a phase response matching the phase response of notch filter 39A is provided to also filter the anti-noise signal. A combiner 36A subtracts the output of notch filter 39A from the output of all-pass filter 39B to generate a signal that represents the information removed from the anti-noise signal by notch filter 39A. The output of combiner 36A is then combined with downlink speech ds before downlink speech ds is provided to filter 34A, preventing the response of notch filter 39A from appearing in the output of combiner 36, since the output of combiner 36A as processed by filter 34A is ideally equal to the change in error microphone signal err due to the presence of notch filter 39A. Reference microphone signal ref is also processed by a notch filter 39C having a copy of the response of N'(z) before processing by filter 34B. The above-described circuit effectively hides the amplitude response of filter 39A from both error microphone signal err and from reference microphone signal ref inputs to W coefficient control block 31, so that W coefficient control circuit 31 does not attempt to adapt the coefficients of adaptive filter 32 to cancel the response of filter 39A, which may be a notch, as described above, or which may be another filter type, such as the low-pass or high-pass filter described above with reference to FIG. 3A.

Figure 3C:
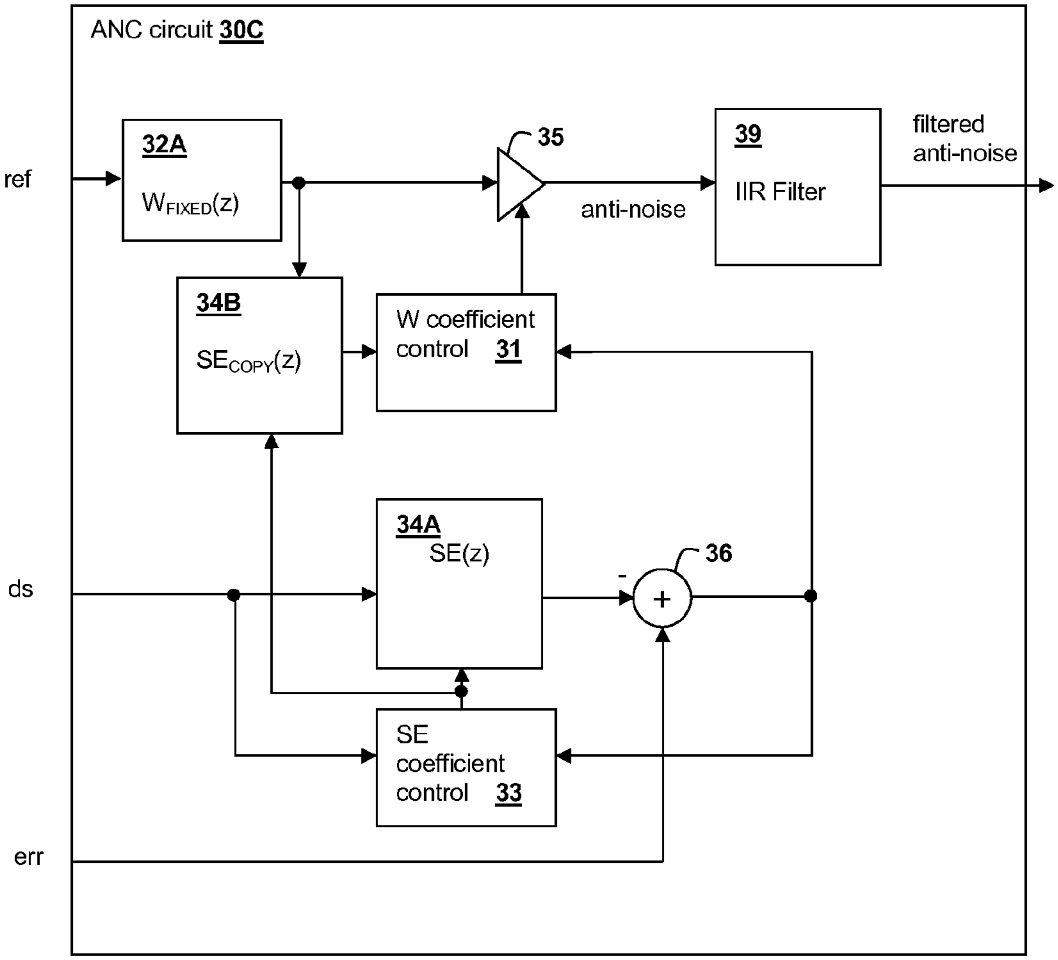

Referring now to FIG. 3C, details of another ANC circuit 30C are shown in accordance with another alternative embodiment of the present invention that may be used to implement ANC circuit 30 of FIG. 2. ANC circuit 30C is similar to ANC circuit 30A of FIG. 3A, so only differences between them will be described below. In ANC circuit 30C, rather than employing an adaptive filter for W(z) in which the entire response is controlled by W coefficient control 31, in ANC circuit 30C, the response of the filter implementing W(z) has only a single gain tap. W coefficient control circuit 31 controls the gain of the anti-noise signal via gain block 35, while the remainder of W(z) is provided by a fixed response filter 32A that implements response $W_{FIXED}(z)$, which is generally a response adapted to the particular design of the personal audio device in a typical acoustic environment. Since the low-frequency gain of W(z) and SE(z) are the components that vary the most due to positioning with respect to the source of acoustic noise and the proximity/pressure of the phone to the ear, providing an adaptive filter with only a gain control for W(z) can prevent introduction of noise boost, since the amplitude response of filter 32A can be very low for other frequencies.

Figure 3D:
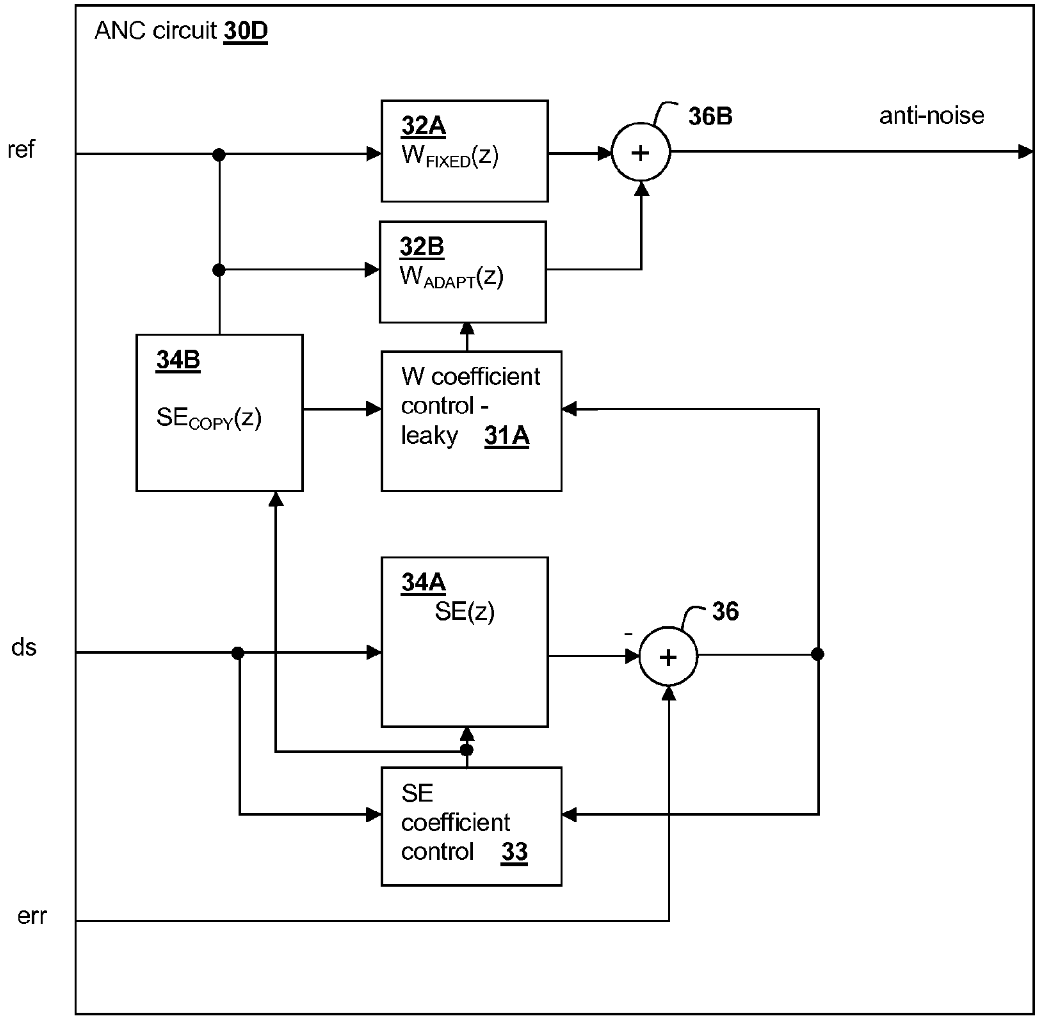

Referring now to FIG. 3D, details of another ANC circuit 30D are shown in accordance with another alternative embodiment of the present invention that may be used to implement ANC circuit 30 of FIG. 2. ANC circuit 30D is similar to ANC circuit 30C of FIG. 3C, so only differences between them will be described below. In ANC circuit 30D, rather than employing a fixed filter for W(z) and only adaptively adjusting the gain applied to the anti-noise signal, in ANC circuit 30D, a fixed response $W_{FIXED}(x)$ is provided by filter 32A and an adaptive portion of the response $W_{ADAPT}(z)$ is provided by adaptive filter 32B, and the outputs of filters 32A and 32B are combined by combiner 36B to provide a total response that has a fixed and an adaptive portion. W coefficient control block 31A has a leaky response, i.e., the response is time-variant such that the response tends over time to a flat frequency response or another predetermined initial frequency response, so that any adaptive change is stabilized by undoing the adaptive change over time.

Figure 3E:
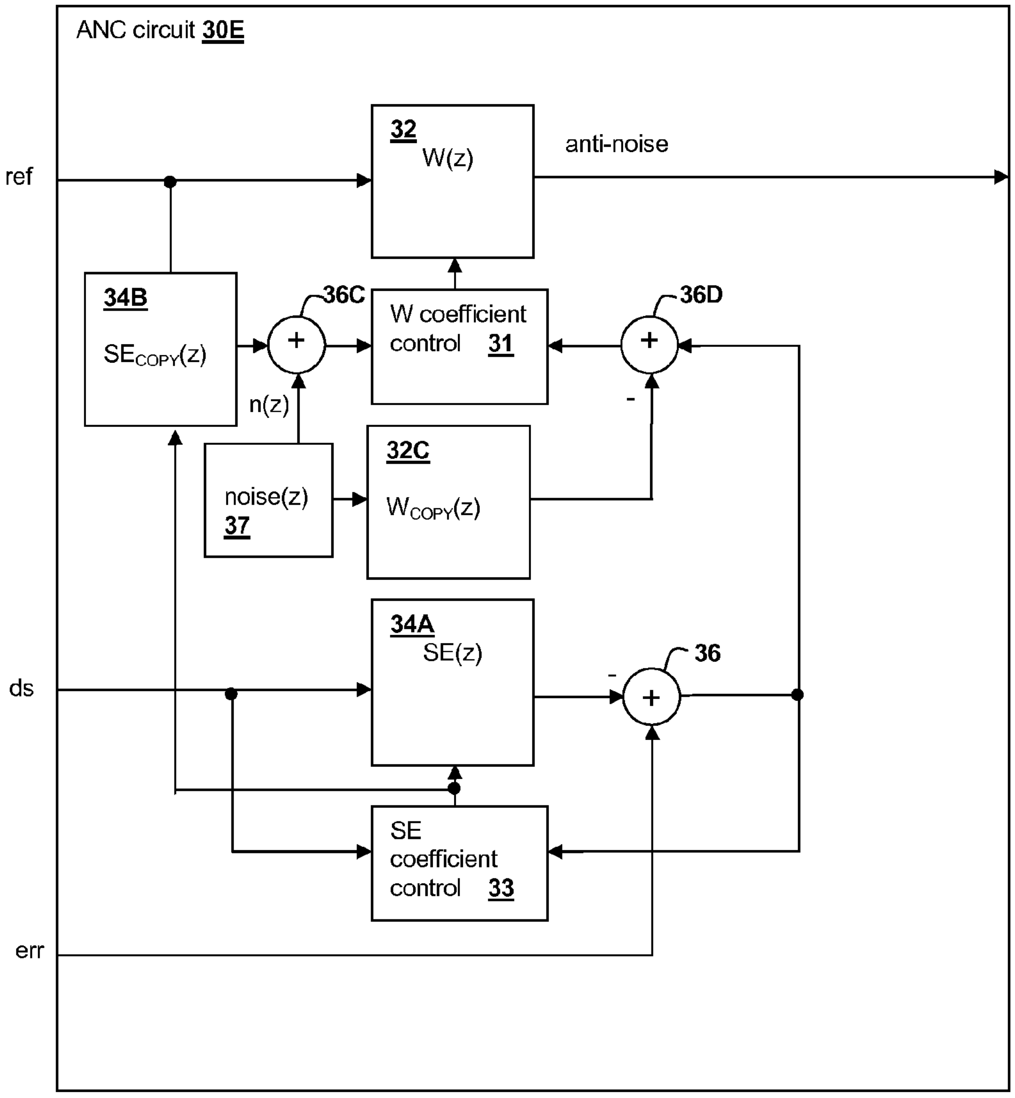

Referring now to FIG. 3E, details of another ANC circuit 30E are shown in accordance with another alternative embodiment of the present invention that may be used to implement ANC circuit 30 of FIG. 2. ANC circuit 30E is similar to ANC circuit 30B of FIG. 3B, so only differences between them will be described below. Rather than removing frequencies from the anti-noise signal using a separate filter as in ANC circuit 30B of FIG. 3B, ANC circuit 30E injects a noise signal noise(z) using a noise generator 37 that is supplied to a copy $W_{COPY}(z)$ of the response W(z) of adaptive filter 32 provided by an adaptive filter 32C. A combiner 36C adds noise signal noise(z) to the output of adaptive filter 34B that is provided to W coefficient control 31. Noise signal n(z), as shaped by filter 32C, is subtracted from the output of combiner 36 by a combiner 36D so that noise signal n(z) is asymmetrically added to the correlation inputs to W coefficient control 31, with the result that the response W(z) of adaptive filter 32 is biased by the completely correlated injection of noise signal n(z) to each correlation input to W coefficient control 31. Since the injected noise appears directly at the reference input to W coefficient control 31, does not appear in error microphone signal err, and only appears at the other input to W coefficient control 31 via the combining of the filtered noise at the output of filter 32C by combiner 36D, W coefficient control will adapt W(z) to attenuate the frequencies present in noise(z). The content of noise signal n(z) does not appear in the anti-noise signal, only in the response W(z) of adaptive filter 32 which will have amplitude decreases at the frequencies/bands in which noise signal n(z) has energy. For example, if it is desirable to decrease the response of W(z) in the vicinity of 1 kHz, noise(z) can be generated to have a spectrum that has energy at 1 kHz, which will cause W coefficient control 31 to decrease the gain of adaptive filter 32 at 1 kHz in an attempt to cancel the apparent source of ambient acoustic sound due to injected noise signal noise(z).

Figure 4A:
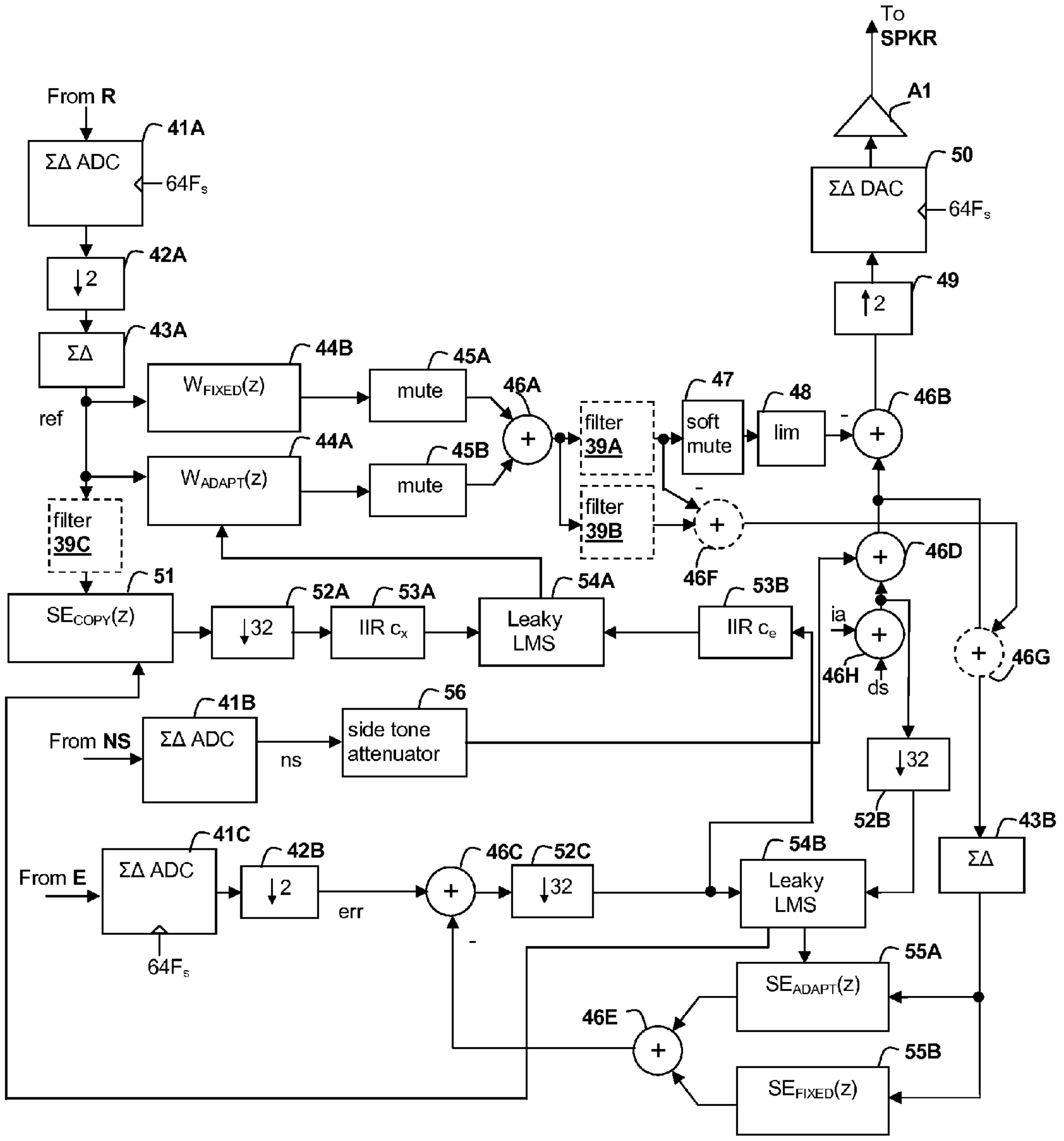
FIG. 4A and FIG. 4B are block diagrams depicting signal processing circuits and functional blocks within integrated circuits in accordance with embodiments of the present invention.

Referring now to FIG. 4A, a block diagram of an ANC system is shown for illustrating ANC techniques in accordance with the embodiments of the invention as illustrated in FIGS. 3A-3D, as may be implemented within CODEC integrated circuit 20. Reference microphone signal ref is generated by a delta-sigma ADC 41A that operates at 64 times oversampling and the output of which is decimated by a factor of two by a decimator 42A to yield a 32 times oversampled signal. A delta-sigma shaper 43A spreads the energy of images outside of bands in which a resultant response of a parallel pair of filter stages 44A and 44B will have significant response. Filter stage 44B has a fixed response $W_{FIXED}(z)$ that is generally predetermined to provide a starting point at the estimate of P(z)/S(z) for the particular design of wireless telephone 10 for a typical user. An adaptive portion $W_{ADAPT}(z)$ of the response of the estimate of P(z)/S(z) is provided by adaptive filter stage 44A, which is controlled by a leaky least-means-squared (LMS) coefficient controller 54A. Leaky LMS coefficient controller 54A is leaky in that the response normalizes to flat or otherwise predetermined response over time when no error input is provided to cause leaky LMS coefficient controller 54A to adapt. Providing a leaky controller prevents long-term instabilities that might arise under certain environmental conditions, and in general makes the system more robust against particular sensitivities of the ANC response. Since LMS coefficient controller 54A has a leaky response, the embodiment of the invention as illustrated in FIG. 3D is included in the system of FIG. 4A. Further, if adaptive filter stage 44A includes only a single gain tap, then the embodiment of the invention as illustrated in FIG. 3C is essentially included in the system of FIG. 4A. Although fixed-response filter 44B in FIG. 4A is arranged in a different circuit arrangement than fixed response filter 32A in FIG. 3C, since the only adaptive portion of the response is either the gain of amplifier 35 or a single tap provided in adaptive filter stage 44A, the adapting of W(z) will occur (and be constrained) in an equivalent manner. Alternatively, or in combination, a notch, low-pass or high-pass filter 39A can be optionally included to filter the anti-noise signal at the output of combiner 46A, as in the embodiment of the invention illustrated in FIG. 3A and FIG. 3B, and all-pass filter 39B and combiner 46F can provide a difference signal that can be added by a combiner 46G to the output of combiner 46D prior to its introduction to filters 55A, 55B as in the embodiment of the invention illustrated in FIG. 3B. Filter 39C is added between the output of delta-sigma shaper 43A and the input to filter 51 when filter 39A is present, so that leaky LMS 54A does not attempt to remove the response of filter 39A from the anti-noise signal by adaptation.

As in the systems of FIGS. 3A-3D, in the system depicted in FIG. 4A, the reference microphone signal is filtered by a copy $SE_{COPY}(z)$ of the estimate of the response of path S(z), by a filter 51 that has a response $SE_{COPY}(z)$, the output of which is decimated by a factor of 32 by a decimator 52A to yield a baseband audio signal that is provided, through an infinite impulse response (IIR) filter 53A to leaky LMS 54A. The error microphone signal err is generated by a delta-sigma ADC 41C that operates at 64 times oversampling and the output of which is decimated by a factor of two by a decimator 42B to yield a 32 times oversampled signal. As in the systems of FIGS. 3A-3D, an amount of downlink audio ds that has been filtered by an adaptive filter to apply response S(z) is removed from error microphone signal err by a combiner 46C, the output of which is decimated by a factor of 32 by a decimator 52C to yield a baseband audio signal that is provided, through an infinite impulse response (IIR) filter 53B to leaky LMS 54A. Response S(z) is produced by another parallel set of filter stages 55A and 55B, one of which, filter stage 55B has fixed response $SE_{FIXED}(z)$, and the other of which, filter stage 55A has an adaptive response $SE_{ADAPT}(z)$ controlled by leaky LMS coefficient controller MB. The outputs of filter stages 55A and 55B are combined by a combiner 46E. Similar to the implementation of filter response W(z) described above, response $SE_{FIXED}(z)$ is generally a predetermined response known to provide a suitable starting point under various operating conditions for electrical/acoustical path S(z). A separate control value is provided in the system of FIG. 4A to control filter 51, which is shown as a single filter stage. However, filter 51 could alternatively be implemented using two parallel stages and the same control value used to control adaptive filter stage 55A could then be used to control the adaptive stage in the implementation of filter 51. The inputs to leaky LMS control block 54B are also at baseband, provided by decimating a combination of downlink audio signal ds and internal audio ia, generated by a combiner 46H, by a decimator 52B that decimates by a factor of 32 after a combiner 46C has removed the signal generated from the combined outputs of adaptive filter stage 55A and filter stage 55B that are combined by another combiner 46E. The output of combiner 46C represents error microphone signal err with the components due to downlink audio signal ds removed, which is provided to LMS control block 54B after decimation by decimator 52C. The other input to LMS control block 54B is the baseband signal produced by decimator 52B.

The above arrangement of baseband and oversampled signaling provides for simplified control and reduced power consumed in the adaptive control blocks, such as leaky LMS controllers 54A and 54B, while providing the tap flexibility afforded by implementing adaptive filter stages 44A-44B, 55A-55B and adaptive filter 51 at the oversampled rates. The remainder of the system of FIG. 4A includes combiner 46H that combines downlink audio ds with internal audio ia, the output of which is provided to the input of a combiner 46D that adds a portion of near-end microphone signal ns that has been generated by sigma-delta ADC 41B and filtered by a sidetone attenuator 56 to prevent feedback conditions. The output of combiner 46D is shaped by a sigma-delta shaper 43B that provides inputs to filter stages 55A and 55B that has been shaped to shift images outside of bands where filter stages 55A and 55B will have significant response.

In accordance with an embodiment of the invention, the output of combiner 46D is also combined with the output of adaptive filter stages 44A-44B that have been processed by a control chain that includes a corresponding hard mute block 45A, 45B for each of the filter stages, a combiner 46A that combines the outputs of hard mute blocks 45A, 45B, a soft mute 47 and then a soft limiter 48 to produce the anti-noise signal that is subtracted by a combiner 46B with the source audio output of combiner 46D. The output of combiner 46B is interpolated up by a factor of two by an interpolator 49 and then reproduced by a sigma-delta DAC 50 operated at the 64× oversampling rate. The output of DAC 50 is provided to amplifier A1, which generates the signal delivered to speaker SPKR.

Figure 4B:
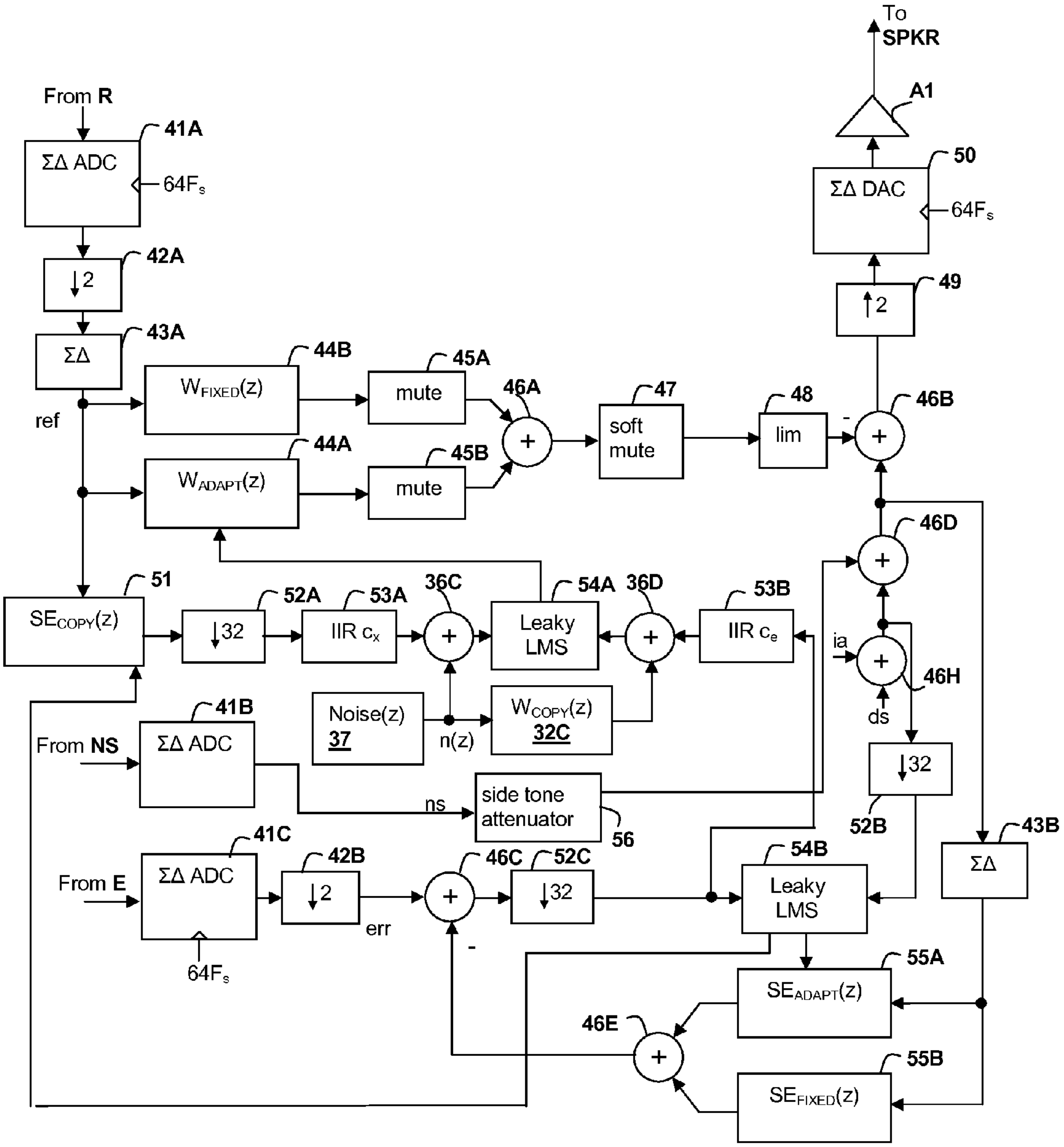

Referring now to FIG. 4B, a block diagram of another ANC system is shown for illustrating ANC techniques in accordance with the embodiment of the invention as illustrated in FIG. 3E, as may be implemented within CODEC integrated circuit 20. The ANC system of FIG. 4B is similar to that of FIG. 4A, so only differences between them will be described in detail below. The ANC system of FIG. 4B includes a noise generator 37 and combiners 36C, 36D that inject noise symmetrically into the correlation inputs of leaky LMS 54A, so that by injecting noise with a particular characteristic, the response of adaptive filter portion 44A which will have amplitude increases at the frequencies/bands in which noise signal n(z) has energy, but so that noise signal n(z) itself does not appear in the anti-noise signal.

Each or some of the elements in the systems of FIG. 4A and FIG. 4B, as well in as the exemplary circuits of FIG. 2 and FIGS. 3A-3E, can be implemented directly in logic, or by a processor such as a digital signal processing (DSP) core executing program instructions that perform operations such as the adaptive filtering and LMS coefficient computations. While the DAC and ADC stages are generally implemented with dedicated mixed-signal circuits, the architecture of the ANC system of the present invention will generally lend itself to a hybrid approach in which logic may be, for example, used in the highly oversampled sections of the design, while program code or microcode-driven processing elements are chosen for the more complex, but lower rate operations such as computing the taps for the adaptive filters and/or responding to detected events such as those described herein.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the personal audio device housing for reproducing an audio signal including both source audio for playback to a listener and an anti-noise signal for countering effects of ambient audio sounds in an acoustic output of the transducer;

a reference microphone mounted on the housing for providing a reference microphone signal indicative of the ambient audio sounds;

an error microphone mounted on the housing in proximity to the transducer for providing an error microphone signal indicative of the acoustic output of the transducer and the ambient audio sounds at the transducer; and a processing circuit that implements an adaptive filter having a response that generates the anti-noise signal from the reference microphone signal to reduce the presence of the ambient audio sounds heard by the listener, wherein the processing circuit shapes the response of the adaptive filter in conformity with the error microphone signal and the reference microphone signal by adapting the response of the adaptive filter to minimize the ambient audio sounds at the error microphone, wherein the response of the adaptive filter is further adjusted independent of the reference microphone signal and independent of the source audio by altering an input to a coefficient control block of the adaptive filter to constrain the adaptive filter to alter the adapting of the adaptive filter to the ambient audio sounds, and wherein the response of the adaptive filter is adjusted independent of the reference microphone signal and the source audio by combining injected noise with the input to the coefficient control block so that the response of the adaptive filter is biased by the coefficient control block adapting to attenuate frequencies present in the injected noise, whereby the response of the adaptive filter is reduced in frequency regions in a frequency range of the injected noise.

2. The personal audio device of claim 1, wherein the response of the adaptive filter is adjusted independent of the reference microphone signal and the source audio by the processing circuit implementing a copy of the adaptive filter to receive the injected noise, and wherein the processing circuit removes an output of the copy of the adaptive filter from the error microphone signal.

3. The personal audio device of claim 1, wherein the processing circuit implements a secondary path adaptive filter having a secondary path response that shapes the source audio and a combiner that removes the shaped source audio from the error microphone signal to provide an error signal indicative of the generated anti-noise delivered to the listener and the ambient audio sounds, and wherein the processing circuit shapes the response of the adaptive filter in conformity with the error signal and the reference microphone signal.

4. A method of canceling ambient audio sounds in proximity of a transducer of a personal audio device, the method comprising:

first measuring ambient audio sounds with a reference microphone to produce a reference microphone signal;

second measuring an output of the transducer and the ambient audio sounds at the transducer with an error microphone;

adaptively generating an anti-noise signal from a result of the first measuring and the second measuring for countering effects of ambient audio sounds at an acoustic output of the transducer by adapting a response of an adaptive filter that filters an output of the reference microphone by adjusting coefficients of the adaptive filter that control the response of the adaptive filter in conformity with an output of the error microphone and the output of the reference microphone by adapting the response of the adaptive filter to minimize the ambient audio sounds at the error microphone;

combining the anti-noise signal with a source audio signal to generate an audio signal provided to the transducer;

adjusting a response of the adaptive filter independent of the reference microphone signal and independent of the source audio signal by altering an input to the adjusting of the coefficients independent of the adaptively generating by combining injected noise with an input to a coefficient control block of the adaptive filter, in order to constrain the adaptive filter to alter the adapting of the adaptive filter to the ambient audio sounds by biasing the response of the adaptive filter by the coefficient control block adapting to attenuate frequencies present in the injected noise, whereby the response of the adaptive filter is reduced in frequency regions in a frequency range of the injected noise; and providing a result of the combining to the transducer to generate the acoustic output.

5. The method of claim 4, wherein the response of the adaptive filter is adjusted independent of the adaptively generating by:

filtering the injected noise with a duplicate response substantially identical to the response of the adaptive filter; and removing a result of the filtering from the error microphone.

6. The method of claim 4, further comprising:

shaping a copy of the source audio signal with a secondary path response;

removing the result of the shaping the copy of the source audio signal from the result of the second measuring to produce an error signal indicative of the generated anti-noise delivered to the listener and the ambient audio sounds; and wherein the adaptively generating generates then anti-noise signal from the result of the first measuring and the error signal.

7. An integrated circuit for implementing at least a portion of a personal audio device, comprising:

an output for providing a signal to a transducer including both source audio for playback to a listener and an anti-noise signal for countering effects of ambient audio sounds in an acoustic output of the transducer;

a reference microphone input for receiving a reference microphone signal indicative of the ambient audio sounds;

an error microphone input for receiving an error microphone signal indicative of the output of the transducer and the ambient audio sounds at the transducer; and a processing circuit that implements an adaptive filter having a response that generates the anti-noise signal from the reference microphone signal to reduce the presence of the ambient audio sounds heard by the listener, wherein the processing circuit shapes the response of the adaptive filter in conformity with the error microphone signal and the reference microphone signal by adapting the response of the adaptive filter to minimize the ambient audio sounds at the error microphone, wherein the response of the adaptive filter is further adjusted independent of the reference microphone signal and independent of the source audio by altering an input to a coefficient control block of the adaptive filter to constrain the adaptive filter to alter the adapting of the adaptive filter to the ambient audio sounds, and wherein the response of the adaptive filter is adjusted by combining injected noise with the input to the coefficient control block so that the response of the adaptive filter is biased by the coefficient control block adapting to attenuate frequencies present in the injected noise, whereby the response of the adaptive filter is reduced in frequency regions in a frequency range of the injected noise.

8. The integrated circuit of claim 7, wherein the response of the adaptive filter is adjusted independent of the reference microphone signal and the source audio by the processing circuit implementing a copy of the adaptive filter to receive the injected noise, and wherein the processing circuit removes an output of the copy of the adaptive filter from the error microphone signal.

9. The integrated circuit of claim 7, wherein the processing circuit implements a secondary path adaptive filter having a secondary path response that shapes the source audio and a combiner that removes the shaped source audio from the error microphone signal to provide an error signal indicative of the generated anti-noise delivered to the listener and the ambient audio sounds, and wherein the processing circuit shapes the response of the adaptive filter in conformity with the error signal and the reference microphone signal.

* * * * *